United States Patent

Parker et al.

[11] Patent Number: 5,583,245
[45] Date of Patent: Dec. 10, 1996

[54] PREPARATION OF SULFUR-CONTAINING ORGANOSILICON COMPOUNDS

[75] Inventors: Dane K. Parker, Massillon; Mark S. Sinsky, Akron, both of Ohio

[73] Assignee: The Goodyear Tire & Rubber Company, Akron, Ohio

[21] Appl. No.: 611,866

[22] Filed: Mar. 6, 1996

[51] Int. Cl.$^6$ .................................. C07F 7/08; C07F 7/18
[52] U.S. Cl. ........................................................ 556/427
[58] Field of Search ............................................. 556/427

[56] References Cited

U.S. PATENT DOCUMENTS

| | | | |
|---|---|---|---|
| 4,507,490 | 3/1985 | Panster et al. | 556/427 |
| 5,399,739 | 3/1995 | French et al. | 556/427 |
| 5,405,985 | 4/1995 | Parker et al. | 556/427 |
| 5,468,893 | 11/1995 | Parker et al. | 556/427 |
| 5,489,701 | 2/1996 | Childress et al. | 556/427 |

*Primary Examiner*—Paul F. Shaver
*Attorney, Agent, or Firm*—Bruce J. Hendricks

[57] ABSTRACT

The present invention relates to a process for the production of organosilicon compounds of the formula $$Z\text{-}Alk\text{-}S_n\text{-}Alk\text{-}Z \qquad (I)$$

in which Z is selected from the group consisting of

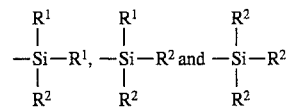

where $R^1$ is an alkyl group of 1 to 4 carbon atoms, cyclohexyl or phenyl;
   $R^2$ is alkoxy of 1 to 8 carbon atoms, or cycloalkoxy of 5 to 8 carbon atoms;
   Alk is a divalent hydrocarbon of 1 to 18 carbon atoms and n is an integer of 2 to 8; comprising reacting (A) a compound of the formula:

$$Z\text{-}Alk\text{-}X \qquad (II)$$

when X is Cl or Br; with (B) an ammonium hydrosulfide or alkali metal hydrosulfide and (C) sulfur;
   wherein the reaction is conducted in the presence of a phase transfer catalyst and an aqueous phase.

17 Claims, No Drawings

PREPARATION OF SULFUR-CONTAINING ORGANOSILICON COMPOUNDS

BACKGROUND

Sulfur containing organosilicon compounds are useful as reactive coupling agents between rubber and silica fillers providing for improved physical properties. They are also useful as adhesion primers for glass, metals and other substrates.

U.S. Pat. Nos. 3,842,111, 3,873,489 and 3,978,103 disclose the preparation of various sulfur containing organosilicon compounds. These organosilicon compounds are prepared by reacting (1) 2 moles of a compound of the formula $$Z\text{-Alk-hal}$$

where hal is a chlorine, bromine or iodine; Z is $$-\underset{\underset{R^2}{|}}{\overset{\overset{R^1}{|}}{Si}}-R^1, \quad -\underset{\underset{R^2}{|}}{\overset{\overset{R^1}{|}}{Si}}-R^2 \text{ or } -\underset{\underset{R^2}{|}}{\overset{\overset{R^2}{|}}{Si}}-R^2$$

where $R^1$ is an alkyl of 1 to 4 carbon atoms or phenyl and $R^2$ is alkoxy of 1 to 8 carbon atoms, cycloalkoxy of 5 to 8 carbon atoms or alkylmercapto with 1 to 8 carbon atoms; Alk is a divalent aliphatic hydrocarbon or unsaturated hydrocarbon or a cyclic hydrocarbon containing 1 to 18 carbon atoms; with (2) 1 mole of a compound of the formula $$Me_2S_n$$

where Me is ammonium or a metal atom and n is a whole number from 2 to 6. Since the two starting materials are liquid, the reaction can take place in the absence of a solvent; however, a volatile inert organic solvent is not only generally used but is preferred. The reaction is carried out with the exclusion of water. The reason for the exclusion of water is to avoid the alkaline hydrolysis reaction of the silyl alkoxy groups which will ultimately lead to insoluble polymeric by-products and lower the overall yield of desired product. Representative organic solvents include aliphatic alcohols such as methyl alcohol and ethyl alcohol. At the end of the reaction between the two starting materials, the separated salt is removed by filtration. The filtrate is then freed from the solvent by distillation under vacuum. Unfortunately, this process suffers from many practical problems. Many of these problems relate to the solvent, e.g. ethyl alcohol. Ethyl alcohol has a low flash point. In addition, it is difficult to obtain and maintain in the water-free (anhydrous) state.

SUMMARY OF THE INVENTION

The present invention relates to a process for the production of sulfur containing organosilicon compounds. The process involves reacting (A) a haloalkylsilane compound with (B) an ammonium hydrosulfide or alkali metal hydrosulfide and (C) sulfur.

DETAILED DESCRIPTION OF THE INVENTION

There is disclosed a process for the production of organosilicon compounds of the formula $$Z\text{-Alk-}S_n\text{-Alk-}Z \quad (I)$$

in which Z is selected from the group consisting of $$-\underset{\underset{R^2}{|}}{\overset{\overset{R^1}{|}}{Si}}-R^1, \quad -\underset{\underset{R^2}{|}}{\overset{\overset{R^1}{|}}{Si}}-R^2 \text{ and } -\underset{\underset{R^2}{|}}{\overset{\overset{R^2}{|}}{Si}}-R^2$$

where $R^1$ is an alkyl group of 1 to 4 carbon atoms, cyclohexyl or phenyl;

$R^2$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8; comprising reacting (A) a compound of the formula:

$$Z\text{-Alk-X} \quad (II)$$

when X is Cl or Br; with (B) an ammonium hydrosulfide or alkali metal hydrosulfide and (C) sulfur;

wherein the reaction is conducted in the presence of a phase transfer catalyst and an aqueous phase.

Examples of sulfur containing organosilicon compounds which may be prepared in accordance with the present invention include: 3,3'-bis(trimethoxysilylpropyl) disulfide, 3,3'-bis(triethoxysilylpropyl) tetrasulfide, 3,3'-bis(triethoxysilylpropyl) octasulfide, 3,3'-bis(trimethoxysilylpropyl) tetrasulfide, 2,2'-bis(triethoxysilylethyl) tetrasulfide, 3,3'-bis(t-rimethoxysilylpropyl) trisulfide, 3,3'-bis(triethoxysilylpropyl) trisulfide, 3,3'-bis(tributoxysilylpropyl) disulfide, 3,3'-bis(trimethoxysilylpropyl) hexasulfide, 3,3'-bis(trimethoxysilylpropyl) octasulfide, 3,3'-bis(trioctoxysilylpropyl) tetrasulfide, 3,3'-bis(trihexoxysilylpropyl) disulfide, 3,3'-bis(tri-2"-ethylhexoxysilylpropyl) trisulfide, 3,3'-bis(triisooctoxysilylpropyl) tetrasulfide, 3,3'-bis(tri-t-butoxysilylpropyl) disulfide, 2,2'-bis(methoxy diethoxy silyl ethyl) tetrasulfide, 2,2'-bis(tripropoxysilylethyl) pentasulfide, 3,3'-bis(tricyclonexoxysilylpropyl) tetrasulfide, 3,3'-bis(tricyclonexoxysilylpropyl) trisulfide, 2,2'-bis(tri-2"-methylcyclohexoxysilylethyl) tetrasulfide, bis(trimethoxysilylmethyl) tetrasulfide, 3-methoxy ethoxy propoxysilyl 3'-diethoxybutoxy-silylpropyltetrasulfide, 2,2'-bis(dimethyl methoxysilylethyl) disulfide, 2,2'-bis(dimethyl sec.butoxysilylethyl) trisulfide, 3,3'-bis(methyl butylethoxysilylpropyl) tetrasulfide, 3,3'-bis(di t-butylmethoxysilylpropyl) tetrasulfide, 2,2'-bis(phenyl methyl methoxysilylethyl) trisulfide, 3,3'bis(diphenyl isopropoxysilylpropyl) tetrasulfide, 3,3'-bis(diphenyl cyclohexoxysilylpropyl) disulfide, 3,3'-bis(dimethyl ethylmercaptosilylpropyl) tetrasulfide, 2,2'-bis(methyl dimethoxysilylethyl) trisulfide, 2,2'-bis(methyl ethoxypropoxysilylethyl) tetrasulfide, 3,3'-bis(diethyl methoxysilylpropyl) tetrasulfide, 3,3'-bis(ethyl di-sec.butoxysilylpropyl) disulfide, 3,3'-bis(propyl diethoxysilylpropyl) disulfide, 3,3'-bis(butyl dimethoxysilylpropyl) trisulfide, 3,3'-bis(phenyl dimethoxysilylpropyl) tetrasulfide, 3-phenyl ethoxybutoxysilyl 3'-trimethoxysilylpropyl tetrasulfide, 4,4'-bis(trimethoxysilylbutyl) tetrasulfide, 6,6'-bis(triethoxysilylhexyl) tetrasulfide, 12,12'-bis(triisopropoxysilyl dodecyl) disulfide, 18,18'-bis(trimethoxysilyloctadecyl) tetrasulfide, 18,18'-bis(tripropoxysilyloctadecenyl) tetrasulfide, 4,4'-bis(trimethoxysilyl-buten-2-yl) tetrasulfide, 4,4'-bis(trimethoxysilylcyclohexylene) tetrasulfide, 5,5'-bis(dimethoxymethylsilylpentyl) trisulfide, 3, 3'-bis(trimethoxysilyl-2-methylpropyl) tetrasulfide and 3,3'-bis(dimethoxyphenylsilyl-2-methylpropyl) disulfide.

The preferred sulfur containing organosilicon compounds which are prepared in accordance with the present invention are the 3,3'-bis(trimethoxy or triethoxy silylpropyl) polysulfides. The most preferred compound is 3,3'-bis(triethoxysilylpropyl) disulfide. Therefore as to formula I, preferably Z is

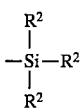

where $R^2$ is an alkoxy of 2 to 4 carbon atoms, with 2 carbon atoms being particularly preferred; Alk is a divalent hydrocarbon of 2 to 4 carbon atoms with 3 carbon atoms being particularly preferred; and n is an integer of from 2 to 6 with 2 being particularly preferred.

With respect to the first reactant of formula II used in the present invention, representative examples include the halogenated (chloro and bromo) substituted forms of ethyl triethoxy silane, propyl triethoxy silane, butyl triethoxy silane, pentyl triethoxy silane, hexyl triethoxy silane, heptyl triethoxy slane, actyl triethoxy silane, nonyl triethoxy slane, decyl triethoxy silane, undecyl triethoxy silane, dodecyl triethoxy silane, tridecyl triethoxy silane, tetradecyl triethoxy silane and penta triethoxy silane to name a few.

The second reactant in the present process is an ammonium hydrosulfide or alkali metal hydrosulfide. Representative metals include potassium, sodium, rubidium or cesium. Preferably, the alkali metal is sodium. Specific examples of such compounds include $C_5HS$, $KHS$, $NaHS$, $NaHS \cdot 2H_2O$, $NaHS \cdot 3H_2O$ and $NH_4HS$.

By varying the molar ratio of the compound of formula II to the hydrosulfide, one can control the resultant reaction product. Generally speaking, the molar ratio of the compound of formula II to hydrosulfide ranges from 1:1 to greater than 1:5. If one desires a higher concentration of a disulfide product, one uses a molar ratio of 1:3 or greater. If one desires a higher concentration of a tetrasulfide product, one uses a lower molar excess of hydrosulfide.

The third compound used in the present invention is sulfur, $S_8$. It is believed that the sulfur may first react with the hydrosulfide to form an intermediate with subsequent reaction of the intermediate with the haloalkylsilane. It is believed that the higher the molar ratio of sulfur to the hydrosulfide, the greater the tendency will be toward formation of the products when n is a higher integer.

By varying the molar ratio of the sulfur to hydrosulfide, one can control the resultant reaction product. Generally speaking, the molar ratio of the sulfur to hydrosulfide ranges from 4:1 to 1:28. If one desires a higher concentration of a disulfide product, one uses a molar excess of hydrosulfide, such as a molar ratio of 1:16. If one desires a higher concentration of a tetrasulfide product, one uses a higher concentration of sulfur; for example, 1:1 to 4:1.

The reaction is conducted in the presence of a phase transfer catalyst. Representative phase transfer catalysts may have a quaternary onium cation of the following structural formulae (III), (IV) or (V):

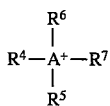 (III)

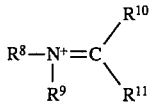 (IV)

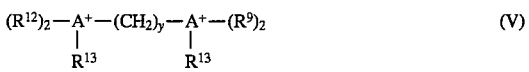 (V)

wherein A represents nitrogen, phosphorus or arsenic; $R^4$, $R^5$, $R^6$, $R^7$, which may be the same or different, are each a linear or branched chain alkyl radical containing from 1 to 16 carbon atoms, optionally substituted with a phenyl, hydroxyl, halo, nitro, alkoxy or alkoxycarbonyl substituent; a linear or branched chain alkenyl radical containing from 2 to 12 carbon atoms, preferably from 4 to 8 carbon atoms and most preferably an alkenyl radical derived from the starting material conjugated diene; an aryl radical containing from 6 to 10 carbon atoms, optionally substituted by one or more alkyl substituents containing from 1 to 4 carbon atoms or alkoxy, alkoxycarbonyl or halo substituents; and with the proviso that any two of said radicals $R^4$ to $R^7$ may together form a single linear or branched chain alkylene, alkenylene or alkadienylene radical containing from 3 to 6 carbon atoms, $R^8$, $R^9$, $R^{10}$, $R^{11}$, which also may be the same or different, are each a linear or branched chain alkyl radical containing from 1 to 4 carbon atoms; with the proviso that the $R^{10}$, and $R^{11}$ radicals may together form an alkylene radical containing from 3 to 6 carbon atoms; and with the further proviso that the $R^9$ and $R^{10}$ or $R^9$ and $R^{11}$ radicals may together forman alkylene, alkenylene or alkadienylene radical containing 4 carbon atoms and, together with the nitrogen atom, comprising a 5-membered nitrogen heterocycle; $R^{12}$ is a linear or branched chain alkyl radical containing from 1 to 4 carbon atoms, or a phenyl radical; $R^{13}$ is a linear or branched chain alkyl radical containing from 1 to 4 carbon atoms, and which may be the same or different from $R^{12}$, a linear or branched chain alkenyl radical containing from 2 to 12 carbon atoms, preferably from 4 to 8 carbon atoms, and more preferably an alkenyl radical derived from the starting material conjugated diene to be carbonylated; and y is an integer of from 1 to 10, and preferably less than or equal to 6.

Exemplary of the quaternary onium cations having the structural Formula III, the following are representative: tetramethylammonium, triethylmethylammonium, tributylmethylammonium, trimethyl(n-propyl)ammonium, tetraethylammonium, tetrabutylammonium, dodecyltrimethylammonium, methyltrioctylammonium, heptyltributylammonium, tetrapropylammonium, tetrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium, hexadecyltrimethylammonium, benzyltrimethylammonium, benzyldimethylpropylammonium, benzyldimethyloctylammonium, benzyltributylammonium, benzyltriethylammonium, phenyltrimethylammonium, benzyldimethyltetradecylammonium, benzyldimethylhexadecylammonium, dimethyldiphenylammonium, methyltrialkyl($C_8$–$C_{10}$) ammonium, methyltriphenylammonium, buten-2-yltriethylammonium, N,N-dimethyl-tetramethyleneammonium, N,N-diethyl-tetramethyleneammonium, tetramethylphosphonium, tetrabutylphosphonium, ethyltrimethylphosphonium, trimethylpentylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri(isopropyl)phosphonium, methyl-tri(n-propyl) phosphonium, methyl-tri(n-butyl)phosphonium, methyl-tri(2-methylpropyl) phosphonium, methyltricyclohexylphosphonium, methyltriphenylphosphonium, methyltribenzyl phosphonium, methyl-tri(4-methylphenyl)phosphonium, methyltrixylylphosphonium, diethylmethylphenylphosphonium, dibenzylmethylphenylphosphonium, ethyltriphenylphosphonium, tetraethylphosphonium, ethyl-tri(n-propyl)phosphonium, triethylpentylphosphonium, hexadecyltributylphosphonium, ethyltriphenylphosphonium, n-butyl-tri(n-propyl)phosphonium, butyltriphenylphosphonium, benzyltriphenylphosphonium, (β-phenylethyl)dimethylphenylphosphonium, tetraphenylphosphonium, triphenyl(4-methylphenyl)phosphonium, tetrakis(hydroxymethyl)phosphonium, tetrakis(2-hydroxyethyl)phosphonium and tetraphenylarsonium.

And exemplary of the Formula V cations are the following: N-methylpyridinium, N-ethylpyridinium, N-hexadecylpyridinium and N-methylpicolinium.

Among the cations having the structural Formula V, the following are representative: 1,2-bis (trimethylammonium)ethane, 1,3-bis (trimethylammonium)propane, 1,4-bis (trimethylammonium)butane and 1,3-bis (trimethylammonium)butane.

Representative of the anions of said onium salts include the following ions: $F^-$, $ClO_4^-$, $PF_6^-$, $BF_4^-$, tetraphenylborate anion, $PO_4^{-3}$, $HPO_2^{-2}$, $H_2PO_4^-$, $CH_3SO_3^-$,

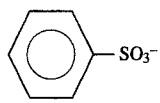

$HSO_4^-$, $NO_3^-$, $SO_4^{-2}$, $Cl^-$, and $Br^-$. Preferably, the anion is $Cl^-$ or $Br^-$.

A particularly preferred onium salt that is used is tetrabutyl ammonium bromide.

The amount of onium salt that is used in the process of the present invention may vary. Generally speaking, the amount of onium salt will range from about 0.1 to 10 mol percent, relative to the compound of formula II, with a range of from 1 to 5 mole percent being preferred.

Wherein the phase transfer catalyst may be added to the reaction at any time, from a practical standpoint, the catalyst is preferably added to the reaction mixture all at once or portionwise at a temperature between 65°–90° C. as a solid or concentrated (40–50%) aqueous solution.

The process of the present invention uses an aqueous system, however, one may optionally use a two phase aqueous/organic system. In fact, it is preferred to use an aqueous/organic system because the presence of the organic phase assists in the phase separation upon completion of the reaction. When the organic phase is used, preferably the silane compound is predissolved in the organic phase prior to addition to the hydrosulfide and sulfur. Representative examples of organic solvents include toluene, xylene, benzene, heptane, octane, decane, chlorobenzene and the like.

As mentioned above, the process of the present invention is conducted in the presence of an aqueous phase. The volume of water that is present may vary. Preferably, the ammonium hydrosulfide or alkali metal hydrosulfide and sulfur are substantially dissolved or dispersed in the aqueous phase prior to reaction with the silane compound of formula II. The concentration of the two reactants in the aqueous phase generally ranges from about 20 to 50 percent by weight. Preferably, the concentration of the sulfide and sulfur in the aqueous phase ranges from about 25 to 45 percent.

The process of the present invention is preferably conducted in the presence of an aqueous phase and a salt of the formula $$X Y \qquad\qquad\qquad\qquad VI$$

or $$X_2SO_4 \qquad\qquad\qquad\qquad VII$$

wherein X is selected from the group consisting of Li, Na, K, Rb and $C_S$; and wherein Y is selected from the group consisting of F, Cl and Br. Representative examples of such salts include LiF, LiCl, LiBr, $Li_2SO_4$, NaF, NaCl, NaBr, $Na_2SO_4$, KF, KCl, KBr, $K_2SO_4$, RbCl, RbBr, $Rb_2SO_4$, CsCl, CsBr and $Cs_2SO_4$. Whereas the amount of salt may vary, the salt is generally present in an amount ranging from 10 percent by weight of the aqueous solution to full or complete saturation of the aqueous solution. Obviously, an excess of salt (more than full saturation) may be used; however, no additional benefit has been found. In addition, as one can appreciate, all of the various salts mentioned above have varying levels of solubility in an aqueous solution; however, the solubility of such salts are well known. In the context of saturation of the aqueous phase, it should be calculated at the desired reaction temperature since solubility of such salts in an aqueous phase are related to the temperature of the aqueous phase. Preferably, the amount of salt that is present in the aqueous phase ranges from 20 weight percent to complete or full saturation. The salt may be added to the reaction vessel at any time so long as it is present during the reaction.

In accordance with the preferred embodiment of the present invention, the hydrosulfide, sulfur and salt are dissolved or dispersed in the aqueous phase. A solvent such as toluene or xylene is then added, followed by the silane compound of formula II. The mixture is then heated, optionally under an inert atmosphere. The mixture may be heated to a temperature ranging from about 60° to 100° C., with a temperature of from 75° to 95° C. being preferred. The appropriate amount of phase transfer catalyst is then added to the reaction mixture as a solid or as a concentrated aqueous solution. The progress of the reaction may then be followed by G.C. or other analytical techniques. Upon filtration, the filtrate is separated into the aqueous phase and organic phase containing the desired product. Any unreacted reagents and/or solvent are removed from the organic phase by stripping at reduced pressure to yield the desired product as the pot residue.

In addition to the hydrosulfide, sulfur and silane, an additional reactant of the formula:

$$Alk\text{-}X \qquad\qquad\qquad\qquad (VIII)$$

where X is previously defined may be present in those instances where unsymmetrical organosilicon compounds are desired in addition to those bis organosilicon compounds previously described.

The unsymmetrical organosilicon compounds are of the formula $$Alk\text{-}S_n\text{-}Alk\text{-}Z \qquad\qquad\qquad\qquad (IX)$$

where n, Alk and Z are as previously defined. As can be appreciated, Alk is a divalent hydrocarbon of 1 to 18 carbon atoms; and, therefore, to avoid duplication, the representative list of unsymmetrical compounds incorporate "alkyl" in their name whereas one skilled in the art appreciates it would be methyl, ethyl, propyl, butyl, etc, and up to octyldecyl, depending on the reactants used. Such representative unsymmetrical compounds include: 3-bis(trimethoxysilylpropyl) n-alkyl disulfide, 3-bis(triethoxysilylpropyl) n-alkyl tetrasulfide, 3-bis(triethoxysilylpropyl) n-alkyl octasulfide, 3-bis(trimethoxysilylpropyl) n-alkyl tetrasulfide, 2-bis(triethoxysilylethyl) n-alkyl tetrasulfide, 3-bis(trimethoxysilylpropyl) n-alkyl trisulfide, 3-bis(triethoxysilylpropyl) n-alkyl trisulfide, 3-bis(tributoxysilylpropyl) n-alkyl disulfide, 3-bis(trimethoxysilylpropyl) n-alkyl hexasulfide, 3-bis(trimethoxysilylpropyl) noalkyl octasulfide, 3-bis(trioctoxysilylpropyl) n-alkyl tetrasulfide, 3-bis(trihexoxysilylpropyl) n-alkyl disulfide, 3-bis(triisooctoxYsilylpropyl) n-alkyl tetrasulfide, 3-bis(tri-t-butoxysilylpropyl) n-alkyl disulfide, 2-bis(methoxy diethoxy silyl ethyl) n-alkyl tetrasulfide, 2-bis(tripropoxysilylethyl) n-alkyl pentasulfide, 3-bis(tricyclonexoxysilylpropyl) n-alkyl tetrasulfide, 3-bis(tricyclonexoxysilylpropyl) n-alkyl trisulfide, 2-bis(dimethyl methoxysilylethyl) n-alkyl disulfide, 2-bis(dimethyl sec.butoxysilylethyl) n-alkyl trisulfide, 3-bis(methyl butylethoxysilylpropyl) n-alkyl tetrasulfide, 3-bis(di t-butyl-methoxysilylpropyl) n-alkyl tetrasulfide, 2-bis(phenyl methyl methoxysilylethyl) n-alkyl trisulfide, 3-bis(diphenyl isopropoxysilylpropyl) n-alkyl tetrasulfide, 3-bis(diphenyl cyclohexoxysilylpropyl) n-alkyl disulfide, 3-bis(dimethyl ethylmercaptosilylpropyl) n-alkyl tetrasulfide, 2-bis(methyl dimethoxysilylethyl) n-alkyl trisulfide, 2-bis(methyl ethoxypropoxysilylethyl) n-alkyl tetrasulfide, 3-bis(diethyl methoxysilylpropyl) n-alkyl tetrasulfide, 3-bis(ethyl di-sec.butoxysilylpropyl) n-alkyl disulfide, 3-bis(propyl diethoxysilylpropyl) n-alkyl disulfide, 3-bis(butyl dimethoxysilylpropyl) n-alkyl trisulfide, 3-bis(phenyl dimethoxysilylpropyl) n-alkyl tetrasulfide, 4-bis(trimethoxysilylbutyl) n-alkyl tetrasulfide, 6-bis(triethoxysilylhexyl) n-alkyl tetrasulfide, 12-bis(triisopropoxysilyl dodecyl) n-alkyl disulfide, 18-bis(trimethoxysilyloctadecyl) n-alkyl tetrasulfide, 18-bis(tripropoxysilyloctadecenyl) n-alkyl tetrasulfide, 4-bis(trimethoxysilyl-buten-2-yl) n-alkyl tetrasulfide, 4-bis(trimethoxysilylcyclohexylene) n-alkyl tetrasulfide, 5-bis(dimethoxymethylsilylpentyl) n-alkyl trisulfide, 3-bis(trimethoxysilyl-2methylpropyl) n-alkyl tetrasulfide and 3-bis(dimethoxyphenylsilyl-2-methylpropyl) n-alkyl disulfide.

This invention is illustrated by the following working example which is presented merely for the purpose of illustration and is not intended to be limiting the scope of the invention. Unless specifically indicated otherwise, parts and percentages are given by weight.

EXAMPLE 1

Control Reaction of 3-Chloropropyltriethoxysilane and Sodium Hydrosulfide

A one liter, three-necked round bottom flask equipped with a mechanical teflon paddle stirrer, a thermometer and a condenser was charged with 45.0 g (0.59 moles) of sodium hydrosulfide flake from PPG® (nominal assay of 73.5 percent as NaSH), 50 ml of saturated sodium chloride solution, 50 ml of toluene and 24.0 g (0.10 moles) of 3-chloropropyltriethoxysilane (CPTES). The mixture was then stirred at 430–470 rpm while heating to 85° C. At this temperature, 1.0 g (0.0031 moles) of tetrabutylammonium bromide phase transfer catalyst was added as a solid all at once to the reaction mixture. No color changes were immediately observed. Within 2 minutes, the lower originally pale yellow aqueous phase had become water white and the temperature of the reaction mixture had risen to about 92° C.

After 15 minutes, the reaction mixture was analyzed by gas chromatography (g.c.) and found to contain 20 percent starting CPTES, 64.9 percent 3-mercaptopropyltriethoxysilane (MPTES), 10.1 percent 3,3'-bis-(triethoxysilylpropyl) monosulfide (TESPM) and 5.0 percent 3,3'-bis-(triethoxysilylpropyl) disulfide (TESPD).

EXAMPLE 2

Reaction of CPTES, NaSH and Sulfur

The reaction as described in Example 1 was repeated except that 0.4 g (0.0125 moles) of elemental sulfur was added to the reaction mixture. Upon addition of the phase transfer catalyst, the reaction mixture became dark green in color. This color fades to a pale yellow-green within 10–15 minutes. After a 15-minute reaction time, g.c. analysis indicated a composition of 12.8 percent starting CPTES, 55.5 percent MPTES, 31.6 percent TESPD and a trace of TESPM.

EXAMPLE 3

Reaction of CPTES, NaSH and Sulfur

The reaction as described in Example 1 was repeated except that 0.8 g (0.025 moles) of elemental sulfur was added to the reaction mixture. Again, a dark green color is observed after the addition of the catalyst. After a 15-minute reaction time, g.c. analysis indicated a composition of 4.4 percent tri-n-butylamine (a catalyst decomposition product), 41.1 MPTES, 52.0 TESPD and 2.5 percent of an unknown. Only trace amounts of CPTES and TESPM were detected.

EXAMPLE 4

Reaction of CPTES, NaSH and Sulfur

The reaction as described in Example 1 was repeated except that 1.2 g (0.0375 moles) of elemental sulfur was added to the reaction mixture. After a 15-minute reaction time, g.c. analysis indicated a composition of 3.7 percent tri-n-butylamine, 19.1 percent MPTES, 77.1 percent TESPD. Trace amounts of CPTES, TESPM and 3,3'-bis-(triethoxysilylpropyl) trisulfide (TESPT) were also detected.

EXAMPLE 5

Reaction of CPTES, NaSH and Sulfur

The reaction as described in Example 1 was repeated except that 1.6 g (0.05 moles) of elemental sulfur was added to the reaction mixture. After a 15-minute reaction time, g.c. analysis indicated a composition of 3.1 percent tri-n-butylamine, 26.3 percent MPTES, 63.0 TESPD and 7.5 TESPT. Trace amounts of CPTES and TESPM were also detected.

EXAMPLE 6

Reaction of CPTES, NaSH and Sulfur

The reaction as ,described in Example 1 was repeated except that 7.8 g (0.10 moles) of PPG® NaSH flake, 3.2 g (0.10 moles) of elemental sulfur and 24.0 g (0.10 moles) of CPTES were used. Upon adding the catalyst at 85° C., the color of the mixture turned dark red which gradually faded to a lighter red over a 30-minute period. Proton and $C^{13}$ nmr analysis of the product indicated a composition of 35 mol percent TESPD, 35 mol percent TESPT and 30 mol percent higher polysulfides.

EXAMPLE 7

Reaction of CPTES, NaSH and Sulfur

The reaction described in Example 1 was repeated except that 7.8 g (0.10 moles) of PPG® NaSH flake, 9.6 g (0.3 moles) of elemental sulfur and 24.0 g (0.10 moles) of CPTES were used. Upon adding the catalyst at 85° C., the color of the mixture turned blackish-red. Reaction was run for 30 minutes at 85° C. The lower aqueous phase became colorless and the upper organic phase, dark red. Proton and $C^{13}$ nmr analysis of the product indicated a composition of 11.8 weight percent TESPD, 28.8 weight percent TESPT, 29.0 weight percent tetrasulfide, 16.5 weight percent pentasulfide, 9.7 weight percent hexasulfide and 4.2 weight percent higher polysulfide.

EXAMPLE 8

Preparation of a Mixture Containinq 3,3'-bis-(triethoxysilylpropyl) disulfide and (3-triethoxysilylpropyl n-butyl disulfide The reaction as described in Example 1 was repeated in a similar manner except that 1.2 g (0.0372 moles) of elemental sulfur was added to the reaction mixture and 12.0 g (0.05 moles) of the original 24.0 g CPTES charge was replaced with 4.65 g (0.05 moles) of 1-chlorobutane. The mixture was heated to 85° C. and 2.0 g of a 50 percent aqueous solution of tetrabutylammoniumbromide (0.0031 moles) were added all at once. The reaction mixture immediately turned greenish-black in color and the reaction temperature increased to about 93° C. before slowly subsiding. After a 30-minute reaction time, the color of the lower aqueous phase had faded to an orangish-green. G.C. analysis of the toluene phase of the mixture indicated a composition of 6.1 percent tri-n-butylamine, 15.3 percent n-butyl disulfide, 6.1 percent MPTES, 45.4 percent of the mixed disulfide, [3-triethoxysilylpropyl] n-butyl disulfide or TEPBD and 27.0 percent TESPD. The colorless toluene phase was separated. The toluene was then removed at reduced pressure to yield 17.85 g of crude product.

EXAMPLE 9

Preparation of a Mixture Containing 3,3'-bis-(triethoxysilylpropyl) disulfide and (3-triethoxysilylpropyl n-butyl disulfide The reaction as described in Example 8 was repeated at a 10× scale. G.C. analysis of the toluene phase of the mixture indicated a composition of 5.9 percent tri-n-butylamine, 14.1 percent n-butyl disulfide, 12.0 percent MPTES, 44.0 percent of the mixed disulfide, [3-triethoxysilylpropyl] n-butyl disulfide, TEPBD and 24.0 percent TESPD. The colorless toluene phase was separated. The toluene was then removed at reduced pressure (27 inches Hg) to yield 158.5 g of crude product. The crude product was then stripped at high vacuum (0.15 mm Hg) to a 110° C. overhead temperature. G.C. analysis of the pot residue indicated a composition of approximately 61.5 percent TEPBD and 38.5 percent TESPD. Pot residue weight was 110 g of an almost colorless liquid.

Upon cooling the orange aqueous phase to room temperature, sodium chloride precipitated. The salt was filtered off and the aqueous phase (854 g) was saved for recycle in Example 10.

EXAMPLE 10

Preparation of a Mixture Containing 3,3'-bis-(triethoxysilylpropyl) disulfide and (3-triethoxysilylpropyl n-butyl disulfide The reaction as described in Example 9 was repeated except that 854 g of aqueous recycle from Example 9 was charged to the reactor along with 76 g of 73.5 percent pure NaSH (1.0 mole) and 12.0 g (0.375 moles) of sulfur. G.C. analysis of the toluene phase of the mixture after reacting for 30 minutes indicated a composition of 6.3 percent tri-n-butylamine, 14.6 percent n-butyl disulfide, 10.6 percent MPTES, 44.4 percent of the mixed disulfide, [3-triethoxysilylpropyl] n-butyl disulfide, TEPBD and 24.1 percent TESPD. The upper toluene/product phase was separated from aqueous phase while the mixture was still warm. Upon cooling the orange aqueous phase to room temperature, sodium chloride precipitated. The salt was filtered off and the aqueous phase (870 g) was saved for recycle in Example 11.

EXAMPLE 11

Preparation of a Mixture Containing 3,3'-bis-(triethoxysilylpropyl) disulfide and (3-triethoxysilylpropyl n-butyl disulfide The reaction as described in Example 9 was repeated except that 870 g of aqueous recycle from Example 10 was charged to the reactor along with 76 g of 73.5 percent pure NaSH (1.0 mole) and 12.0 g (0.375 moles) of sulfur. G.C. analysis of the toluene phase of the mixture after reacting for 30 minutes indicated a composition of 6.0 percent tri-n-butylamine, 14.5 percent n-butyl disulfide, 10.0 percent MPTES, 43.6 percent of the mixed disulfide, (3-triethoxysilylpropyl) n-butyl disulfide, TEPBD and 25.9 percent TESPD. The upper toluene/product phase was separated from aqueous phase while the mixture was still warm. Upon cooling the orange aqueous phase to room temperature, sodium chloride precipitated. The salt was filtered off and the aqueous phase (878 g) was saved for recycle in Example 12.

EXAMPLE 12

Preparation of a Mixture Containing 3,3-bis-(triethoxysillpropyl) disulfide and (3-triethoxysilylpropyl n-butyl disulfide The reaction as described in Example 9 was repeated except that 878 g of aqueous recycle from Example 11 was charged to the reactor along with 76 g of 73.5 percent pure NaSH (1.0 mole) and 12.0 g (0.375 moles) of sulfur. G.C. analysis of the toluene phase of the mixture after reacting for 30 minutes indicated a composition of 6.8 percent tri-n-butylamine, 15.0 percent n-butyl disulfide, 10.3 percent MPTES, 44.0 percent of the mixed disulfide, [3-triethoxysilylpropyl] n-butyl disulfide, TEPBD and 23.9 percent TESPD. The upper toluene/product phase was separated from aqueous phase while the mixture was still warm. Upon cooling the orange aqueous phase to room temperature, sodium chloride precipitated.

These examples demonstrate two things. First, that a high level of a mixed trialkoxysilylpropyl-n-alkyl disulfide (as a statistical mixture) can be readily prepared by this phase transfer technique. Secondly, the aqueous phase can be recycled at least three times to give essentially the same product composition by adding just enough sodium hydrosulfide and sulfur to each recycle to compensate for that converted to disulfides in the previous run.

The mixed disulfides containing trialkoxysilylpropyl-n-alkyl disulfide may provide superior processing and cost advantages in rubber/silica mixes relative to that obtained from more conventional sulfur-containing bis-silanes.

While certain representative embodiment and details have been shown for the purpose of illustrating the invention, it will be apparent to those skilled in the art that various changes and modifications may be made therein without departing from the spirit or scope of the invention.

What is claimed is:

1. A process for the production of organosilicon compounds of the formula $$Z\text{-Alk-}S_n\text{-Alk-}Z \quad (I)$$

in which Z is selected from the group consisting of $$-\underset{\underset{R^2}{|}}{\overset{\overset{R^1}{|}}{Si}}-R^1, \quad -\underset{\underset{R^2}{|}}{\overset{\overset{R^1}{|}}{Si}}-R^2 \text{ and } -\underset{\underset{R^2}{|}}{\overset{\overset{R^2}{|}}{Si}}-R^2$$

where $R^1$ is an alkyl group of 1 to 4 carbon atoms, cyclohexyl or phenyl;

$R^2$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8; comprising reacting (A) a compound of the formula:

$$Z\text{-Alk-}X \quad (II)$$

when X is Cl or Br; with (B) an ammonium hydrosulfide or alkali metal hydrosulfide and (C) sulfur; wherein the reaction is conducted in the presence of a phase transfer catalyst and an aqueous phase.

2. The process of claim 1 wherein Z is:

$$-\underset{\underset{R^2}{|}}{\overset{\overset{R^2}{|}}{Si}}-R^2$$

$^2$ is an alkoxy of 2 to 4 carbon atoms, n is an integer of from 2 to 4, and Alk is a divalent hydrocarbon of 2 to 4 carbon atoms.

3. The process of claim 1 wherein X is Cl.

4. The process of claim 2 wherein R is an alkoxy of 2 carbon atoms.

5. The process of claim 1 wherein the reaction is carried out at a temperature ranging from 60° C. to 100° C.

6. The process of claim 1 wherein the reaction is conducted in the presence of an aqueous phase and an organic phase.

7. The process of claim 1 wherein the phase transfer catalyst is selected from formulae:

$$R^4-\underset{\underset{R^5}{|}}{\overset{\overset{R^6}{|}}{A^+}}-R^7 \quad (III)$$

$$R^8-N^+=C\underset{R^9}{\overset{R^{10}}{\diagup}}\diagdown_{R^{11}} \quad (IV)$$

$$(R^{12})_2-\underset{\underset{R^{13}}{|}}{A^+}-(CH_2)_y-\underset{\underset{R^{13}}{|}}{A^+}-(R^9)_2 \quad (V)$$

wherein A represents nitrogen, phosphorus or arsenic; $R^4$, $R^5$, $R^6$, $R^7$, which may be the same or different are each a linear or branched chain alkyl radical containing from 1 to 16 carbon atoms, optionally substituted with a phenyl, hydroxyl, halo, nitro, alkoxy or alkoxycarbonyl substituent; a linear or branched chain alkenyl radical containing from 2 to 12 carbon atoms; an aryl radical containing from 6 to 10 carbon atoms, optionally substituted by one or more alkyl substituents containing from 1 to 4 carbon atoms or alkoxy, alkoxycarbonyl or halo substituents; and with the proviso that any two of said radicals $R^4$ to $R^7$ may together form a single linear or branched chain alkylene, alkenylene or alkadienylene radical containing from 3 to 6 carbon atoms, $R^8$, $R^9$, $R^{10}$, $R^{11}$, which also may be the same or different, are each a linear or branched chain alkyl radical containing from 1 to 4 carbon atoms; with the proviso that the $R^{10}$, and $R^{11}$radicals may together form an alkylene radical containing from 3 to 6 carbon atoms; and with the further proviso that the $R^9$ and $R^{10}$ or $R^9$ and $R^{11}$ radicals may together form an alkylene, alkenylene or alkadienylene radical containing 4 carbon atoms and, together with the nitrogen atom, comprising a 5-membered nitrogen heterocycle; $R^{12}$ is a linear or branched chain alkyl radical containing from 1 to 4 carbon atoms, or a phenyl radical; $R^{13}$ is a linear or branched chain alkyl radical containing from 1 to 4 carbon atoms, and which may be the same or different from $R^{12}$, a linear or branched chain alkenyl radical containing from 2 to 12 carbon atoms; and y is an integer greater than or equal to 1 and less than or equal to 10.

8. The process of claim 7 wherein said phase transfer catalyst is selected from the group of cations consisting of tetramethylammonium, triethylmethylammonium, tributylmethylammonium, trimethyl(n-propyl)ammonium, tetraethylammonium, tetrabutylammonium, dodecyltrimethylammonium, methyltrioctylammonium, heptyltributylammonium, tetrapropylammonium, etrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium, hexadecyltrimethylammonium, benzyltrimethylammonium, benzyldimethylpropylammonium, benzyldimethyloctylammonium, benzyltributylammonium, benzyldimethyltetradecylammonium, benzyldimethylhexadecylammonium, dimethyldiphenylammonium, methyltrialkyl($C_8$-$C_{10}$) ammonium, methyltriphenylammonium, buten-2-yltriethylammonium, N,N-dimethyl-tetramethyleneammonium, N,N-diethyl-tetramethyleneammonium, tetramethylphosphonium, tetrabutylphosphonium, ethyltrimethylphosphonium, trimethylpentylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri(isopropyl)phosphonium, methyl-tri(n-propyl)phosphonium, methyl-tri(n-butyl)phosphonium, methyl-tri(2-methylpropyl)phosphonium, methyltricyclohexylphosphonium, methyltriphenylphosphonium, methyltribenzyl phosphonium, methyl-tri(4-methylphenyl)phosphonium, methyltrixylylphosphonium, diethylmethylphenylphosphonium, dibenzylmethylphenylphosphonium, ethyltriphenylphosphonium, tetraethylphosphonium, ethyl-tri(n-propyl)phosphonium, triethylpentylphosphonium, hexadecyltributylphosphonium, ethyltriphenylphosphonium, n-butyl-tri(n-propyl)phosphonium, butyltriphenylphosphonium, benzyltriphenylphosphonium, (β-phenylethyl)dimethylphenylphosphonium, tetraphenylphosphonium, triphenyl(4-methylphenyl)phosphonium, tetrakis(hydroxymethyl)phosphonium, tetrakis(2-hydroxyethyl)phosphonium, tetraphenylarsonium, N-methylpyridinium, N-ethylpyridinium, N-hexadecylpyridinium, N-methylpicolinium, 1,3-bis-2-yldimethylammonium)propane, 1,2-bis(trimethylammonium)ethane, 1,3-bis(trimethylammonium)propane, 1,4-bis(trimethylammonium)butane, and 1,3-bis(trimethylammonium)butane and selected from the group of anions consisting of $F^-$, $ClO_4^-$, $PF_6^-$, $BF_4^-$, tetraphenylborate anion, $PO_4^{-3}$, $HPO_4^{-2}$, $H_2PO_4^-$, $CH_3SO_3^-$,

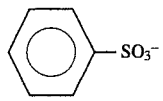

$HSO_4^-$, $NO_3^-$, $SO_4^{-2}$, $Cl^-$, and $Br^-$.

9. The process of claim 1 wherein said phase transfer catalyst is tetrabutyl ammonium bromide.

10. The process of claim 1 wherein said phase transfer catalyst is an onium salt that is present in an amount ranging from 0.1 to 10 mol percent relative to the compound of formula II.

11. The process of claim 6 wherein an organic solvent is selected from the group consisting of toluene, xylene, benzene, heptane, octane, decane, chlorobenzene and the like.

12. The process of claim 11 wherein said organic solvent is toluene.

13. The process of claim 1 wherein the reaction is conducted in the presence of a salt of one of the following formulae $$X Y \qquad \text{VI}$$

or $$X_2SO_4 \qquad \text{VII}$$

wherein X is selected from the group consisting of Li, Na, K, Rb and Cs; and wherein Y is selected from the group consisting of Fl, Cl and Br.

14. The process of claim 13 wherein said salt is NaCl.

15. The process of claim 13 wherein said salt is present in an amount ranging from 10 weight percent of the aqueous solution to full saturation of the aqueous solution.

16. The process of claim 1 wherein, in addition to reactants (A), (B) and (C), a compound (D) is present and is of the formula:

$$Alk\text{-}X \qquad \text{(VIII)}.$$

17. The process of claim 1 wherein the molar ratio of the compound of formula II to the compound of formula VIII ranges from 99:1 to 1:1.

* * * * *